(12) United States Patent
Maschke

(10) Patent No.: US 7,753,852 B2
(45) Date of Patent: *Jul. 13, 2010

(54) ATHERECTOMY CATHETER WITH COMBINED OCT/IVUS IMAGING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 98 days.

This patent is subject to a terminal disclaimer.

(21) Appl. No.: 11/526,178

(22) Filed: Sep. 22, 2006

(65) Prior Publication Data

US 2007/0066890 A1 Mar. 22, 2007

(30) Foreign Application Priority Data

Sep. 22, 2005 (DE) .................. 10 2005 045 373

(51) Int. Cl.
*A61B 8/12* (2006.01)
(52) U.S. Cl. ................ 600/471; 600/439; 600/478
(58) Field of Classification Search ........... 600/407, 600/424, 427, 439, 476–480, 471; 606/159
See application file for complete search history.

(56) References Cited

U.S. PATENT DOCUMENTS

| | | | | |
|---|---|---|---|---|
| 5,287,858 | A | * | 2/1994 | Hammerslag et al. ....... 600/585 |
| 5,391,199 | A | | 2/1995 | Ben-Haim |
| 5,540,959 | A | | 7/1996 | Wang |
| 5,638,819 | A | | 6/1997 | Manwaring et al. |
| 5,752,513 | A | | 5/1998 | Acker et al. |
| 5,769,087 | A | * | 6/1998 | Westphal et al. ............ 600/573 |
| 5,830,145 | A | * | 11/1998 | Tenhoff ...................... 600/463 |
| 5,865,748 | A | | 2/1999 | Co et al. |
| 5,895,402 | A | | 4/1999 | Hundertmark et al. |
| 5,897,529 | A | * | 4/1999 | Ponzi ...................... 604/95.04 |
| 6,148,095 | A | * | 11/2000 | Prause et al. ................ 382/131 |
| 6,152,878 | A | | 11/2000 | Nachtomy et al. |
| 6,217,527 | B1 | * | 4/2001 | Selmon et al. .............. 600/585 |
| 6,233,476 | B1 | | 5/2001 | Strommer et al. |
| 6,298,261 | B1 | | 10/2001 | Rex |
| 6,299,622 | B1 | * | 10/2001 | Snow et al. ................. 606/159 |
| 6,366,799 | B1 | | 4/2002 | Acker et al. |
| 6,506,972 | B1 | | 1/2003 | Wang |
| 6,546,271 | B1 | | 4/2003 | Reisfeld |
| 6,673,999 | B1 | | 1/2004 | Wang et al. |
| 6,713,671 | B1 | | 3/2004 | Wang et al. |
| 6,772,001 | B2 | | 8/2004 | Maschke |
| 6,788,967 | B2 | | 9/2004 | Ben-Haim et al. |

(Continued)

FOREIGN PATENT DOCUMENTS

DE 40 37 586 A1 5/1992

(Continued)

OTHER PUBLICATIONS

Biophan Technologies Inc., "MRI Shielding for Medical Devices", p. 1-5, Retrieved from Internet on Nov. 7, 2005, http://www.biophan.com/shielding.php.

(Continued)

*Primary Examiner*—Brian Casler
*Assistant Examiner*—Jonathan G Cwern

(57) ABSTRACT

Catheter device for performing atherectomy, comprising an atherectomy catheter, an OCT sensor, an IVUS sensor, position sensors and an image processing unit, which is embodied for creating combined 2D and/or 3D images based on the data of the sensors.

18 Claims, 4 Drawing Sheets

U.S. PATENT DOCUMENTS

| | | |
|---|---|---|
| 6,813,512 B2 | 11/2004 | Aldefeld et al. |
| 2001/0031919 A1 | 10/2001 | Strommer et al. |
| 2002/0019644 A1* | 2/2002 | Hastings et al. ............. 606/159 |
| 2002/0049375 A1 | 4/2002 | Strommer et al. |
| 2002/0087208 A1* | 7/2002 | Koblish et al. .............. 607/113 |
| 2003/0080284 A1* | 5/2003 | Wake et al. ................. 250/221 |
| 2003/0195419 A1* | 10/2003 | Harada ....................... 600/437 |
| 2004/0008882 A1 | 1/2004 | Hornegger et al. |
| 2004/0133106 A1* | 7/2004 | Kakee et al. ................ 600/437 |
| 2005/0101859 A1 | 5/2005 | Maschke |
| 2005/0113685 A1 | 5/2005 | Maschke et al. |
| 2005/0203553 A1* | 9/2005 | Maschke ................... 606/159 |
| 2005/0222595 A1 | 10/2005 | Maschke |
| 2005/0234343 A1 | 10/2005 | Maschke |
| 2006/0015126 A1* | 1/2006 | Sher .......................... 606/159 |
| 2006/0081031 A1* | 4/2006 | Anderson et al. ................ 73/9 |

FOREIGN PATENT DOCUMENTS

| | | |
|---|---|---|
| DE | 695 14 238 | 6/1997 |
| DE | 198 27 460 A1 | 12/1998 |
| DE | 198 52 467 A1 | 7/1999 |
| DE | 100 51 244 | 5/2002 |
| DE | 102 24 011 | 12/2003 |
| DE | 103 54 496 | 7/2005 |
| DE | 10 2004 008 370 | 9/2005 |
| DE | 10 2004 015 642 | 2/2006 |
| DE | 10 2004 015 641 | 3/2006 |
| EP | 0 933 804 A1 | 4/2000 |
| EP | 1 034 738 B1 | 9/2000 |

OTHER PUBLICATIONS

R J Dickinson and R I Kitney, "Miniature Ultrasonic Probe Construction for Minimal Access Surgery", Phys. Med. Biol. 49, 2004, pp. 3527-3538.

H. Von Bibra, D. Bone, J.-U. Voigt, U. Niklasson, B. Wranne, L. Rydén, "Kontrastechokardiographie", Z Kardiol, 2000, pp. I/86-I/96, vol. 89, Suppl. 1.

* cited by examiner

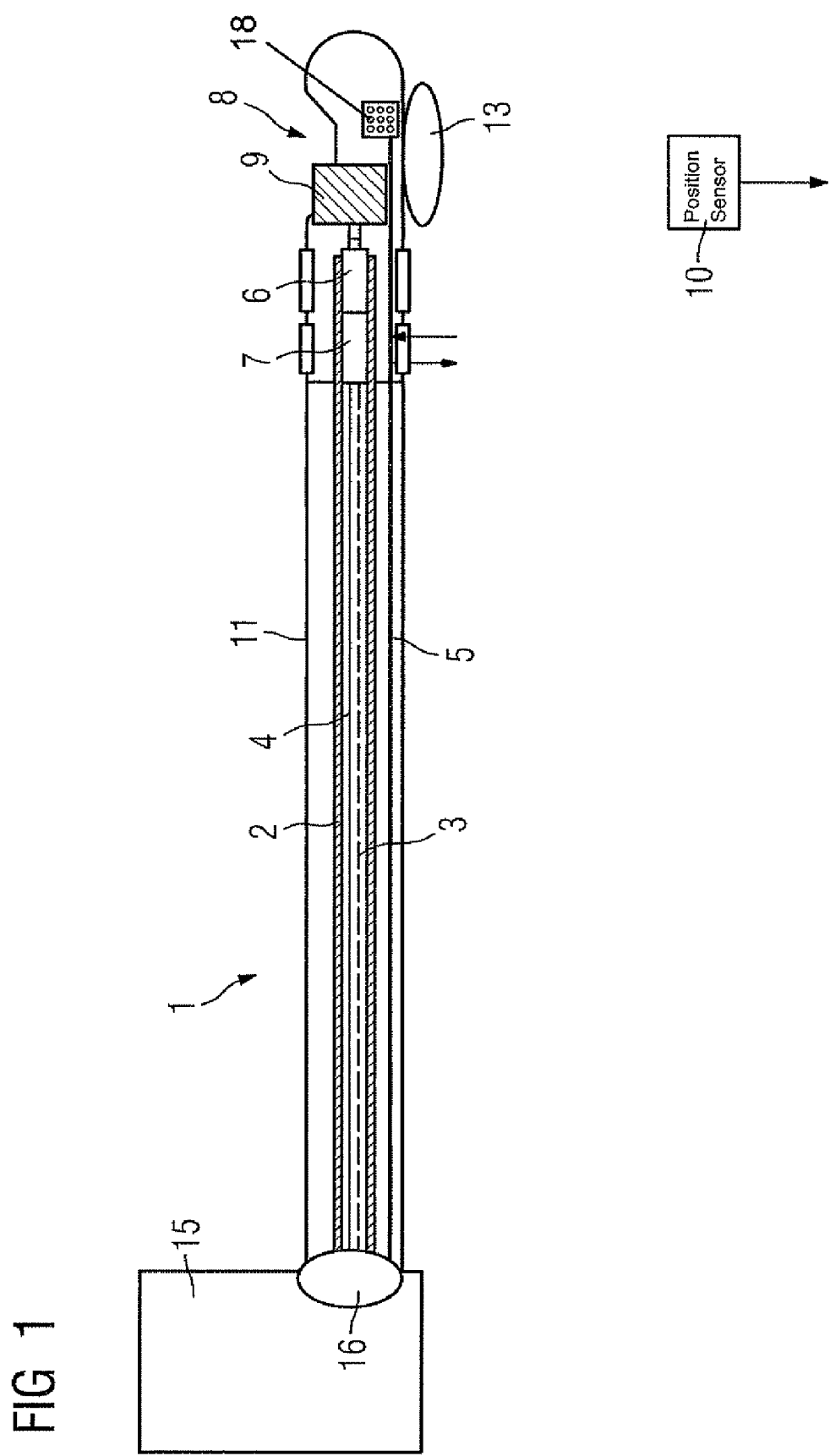

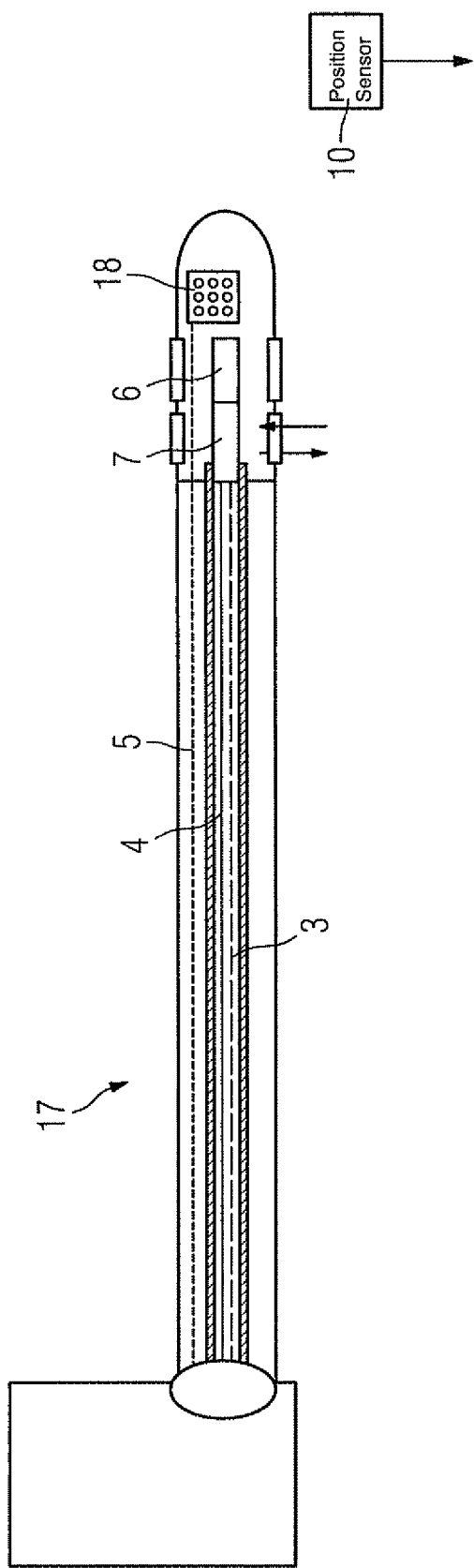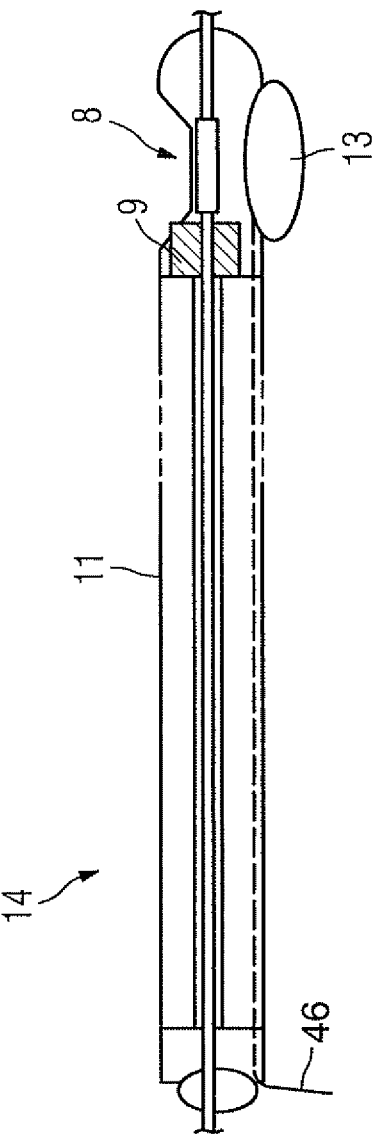
FIG 2A
FIG 2B

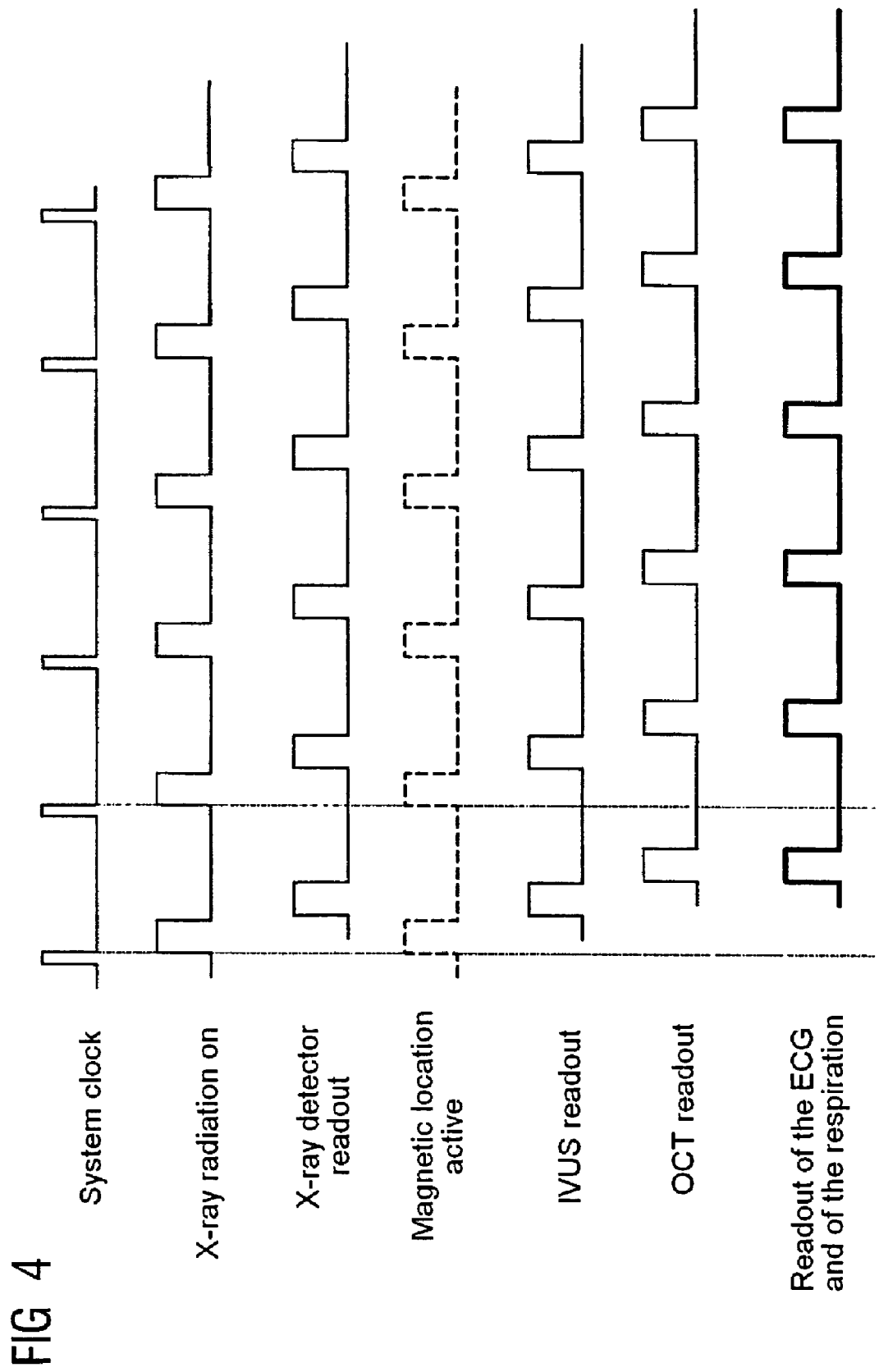

ATHERECTOMY CATHETER WITH COMBINED OCT/IVUS IMAGING

CROSS REFERENCE TO RELATED APPLICATIONS

This application claims priority of German application No. 10 2005 045 373.2 filed Sep. 22, 2005, which is incorporated by reference herein in its entirety.

FIELD OF THE INVENTION

The invention relates to a catheter device for performing an atherectomy.

BACKGROUND OF THE INVENTION

Diseases of the vascular vessels are among the most frequent diseases with fatal outcomes. In particular these include coronary infarction caused by diseases of the coronary vessels. If arteriosclerotic plaque causes an occlusion of coronary vessels, these symptoms are generally treated using Percutaneous Transluminal Coronary Angioplasty (PCTA). The constricted points of the coronary vessels are expanded in such cases with a balloon catheter. However clinical studies have shown that with very many patients a restenosis occurs, in some cases these types of restenosis have occurred in 50% of the patients. High-frequency rotablation angioplasty has been known as an alternative method for a number of years, which can be used advantageously, especially for fibrotic or calcified or extensive stenoses.

To reduce the danger of the formation of restenoses, coronary atherectomy is used in order to achieve a recanalization of stenosized coronary arteries through "debulking". The device for performing the atherectomy is a catheter system with a metal housing which the actual cutting apparatus, referred to as the cutter, is located. The cutter, consisting of conically ground knives, is connected via a flexible connection to a motor outside the patient. The cutting knife is driven by this motor at a speed of 1500-2000 rpm. On one side of the metal housing a balloon is mounted on the contralateral side is a window. In atherectomy the balloon is inflated and thereby the openings and the knife are pushed into the plaque. The rotating knife can now be push forwards from outside against the tip of the atherectomy housing. This cuts out the plaque and the plaque material is pushed onto the tip of the atherectomy device. The balloon is then deflated, the atherectomy device rotated a little, so that the window shows the plaque in another direction, and the process is repeated. An atherectomy device is known from U.S. Pat. No. 5,895,402.

In DE 10 2004 008 370 A1 a catheter with an integrated OCT sensor for use in blood vessels has been proposed, through which the image display in the local area of the restenosis is improved.

A medical examination and treatment system has been proposed by US 2005/0101859 A1 which combines the OCT and IVUS imaging methods in one device. This enables overlaid 2D image recordings to be created, with the OCT image element being used for the local area and the IVUS image element for the remote area.

A medical examination and/or treatment system is known from US 2005/0113685 A1, in which the imaging methods OCT and IVUS are combined in one catheter, which is also provided with a position sensor. 3D images can be created by means of the information recorded by the position sensor.

The factor common to all known solutions however is that they only resolve individual problems in each case, it has not however been possible thus far to integrate the conventional catheter in an optimum way into the medical workflow.

SUMMARY OF THE INVENTION

The underlying problem addressed by the invention is that of specifying a catheter device which is better integrated into the medical workflow and allows optimum diagnostic imaging within the framework of a minimally invasive medical therapy.

To achieve this object, provision is made for an inventive catheter device of the type mentioned at the start to feature a atherectomy catheter, an OCT sensor, an IVUS sensor, position sensors and also an image processing unit which is embodied for creation of combined 2D and/or 3D image recordings based on the data of the sensor.

The invention is based on the knowledge that previously separate known catheters are able to be combined into an integrated unit by using an IVUS sensor, an OCT sensor and also position sensors and the picture information obtained in this way can be overlaid in a 2D presentation used to create a 3D image recording.

The inventive catheter device is preferably integrated into a medical treatment device, especially an x-ray device. Such an angiographic or cardiological x-ray system with high-voltage generator, x-ray source, beam diaphragm, image detector unit, patient table, emitter and detector stands and a digital imaging system makes the creation of angiographic x-ray images as well as optical images possible in the shape of computer tomography images and is able to process, present and overlay the information and recorded images supplied by the inventive catheter device.

A magnetic control, but also alternatively a mechanical control can be provided in the inventive catheter device, which preferably features pulling wires in order to deflect the catheter tip. In this way the tip of the catheter can be deflected to one side.

There can also be provision for controlling the catheter through an external magnetic field, in which case the catheter features at least one permanent magnet and/or at least one electromagnet. In a further embodiment of the invention the receiver coils can have iron cores and optionally be used as receive antenna or as electromagnets for magnetic navigation.

To achieve a miniaturization of the catheter it is not necessary for the coils to be arranged orthogonally in relation to each other, instead they can be disposed at any given angle, especially around 60°.

With the inventive catheter device the OCT sensor and/or the IVUS sensor can be aligned to one side in relation to the longitudinal axis of the catheter. Accordingly the OCT sensor and the IVUS sensor can be rotated separately or together around the longitudinal axis of the catheter. Alternatively however a number of stationary sensors distributed around the circumference can be provided, which are interrogated in turn. It is also possible for the catheter to be advanced and withdrawn at a definable speed by a drive unit. In this way three-dimensional image recordings can be made.

As part of the image processing the image processing unit of the inventive catheter device can be embodied for approximation of the center line and/or of the envelope of the part of the body to be examined, especially of a vessel. The vessel envelope can be used in further image postprocessing steps. For example, with the aid of the envelope the three-dimensional OCT-IVUS images can be registered with other anatomical image data, which originates from a 3D angiography system for example, and can subsequently be shown fused. In this case the 3D images recorded by the catheter and the anatomical image data are expediently transferred to a common coordinate system.

In order to avoid movement artifacts with the inventive catheter device, which arise for example through breathing, the movement of the heart or other organs, the frequency and/or the amplitude of the movement can be recorded and computationally corrected.

To avoid faults in the signals recorded by the sensors, provision can be made for the sensors to be able to be read out offset in time. For example x-ray detectors and an electrocardiogram which may be present are not read out if the transmitters of the electromagnetic position system are active. The OCT sensors and the position sensors are not read out if the x-ray radiation is active. Thus only those signals are detected in each case which are not influenced by faults.

Especially good results can be obtained if the inventive catheter device has a coating to shield it from electromagnetic fields.

Such a coating can be a thin-film layer made of conducting nanoparticles.

To prevent the patient being at risk from mains voltage, the catheter and its sensors can be electrically decoupled from the mains voltage.

To facilitate locating the catheter using x-ray images, the catheter can feature x-ray markers.

To reduce the frictional resistance of the catheter while it is moving within a vessel it can be provided with a coating which preferably consists of a silicon material and/or nanomaterials. To support positioning, the catheter can have an inflatable balloon, especially at its tip.

To output a warning of high temperature if necessary, the catheter can have a temperature senor preferably arranged at its tip, and also a pressure sensor if necessary.

In addition the invention relates to a medical treatment device, especially an x-ray device. The inventive treatment device comprises a catheter device of the type described.

In addition the invention relates to a method for creating examination images when carrying out atherectomy. The inventive method is characterized in that a atherectomy catheter is used which possesses an OCT sensor, an IVUS sensor and position sensors, in which case an image processing unit can be used to create combined 2D and/or 3D recorded images based on the data of the sensors.

BRIEF DESCRIPTION OF THE DRAWINGS

Further advantages and details of the invention are explained on the basis of exemplary embodiments which refer to the figures. The figures are schematic diagrams and show:

FIG. 1 an inventive catheter device for carrying out atherectomy,

FIG. 2 a second exemplary embodiment of an inventive catheter device,

FIG. 4 a schematic diagram of the sensor readout with treatment device of FIG. 3.

DETAILED DESCRIPTION OF THE INVENTION

Figure 3:
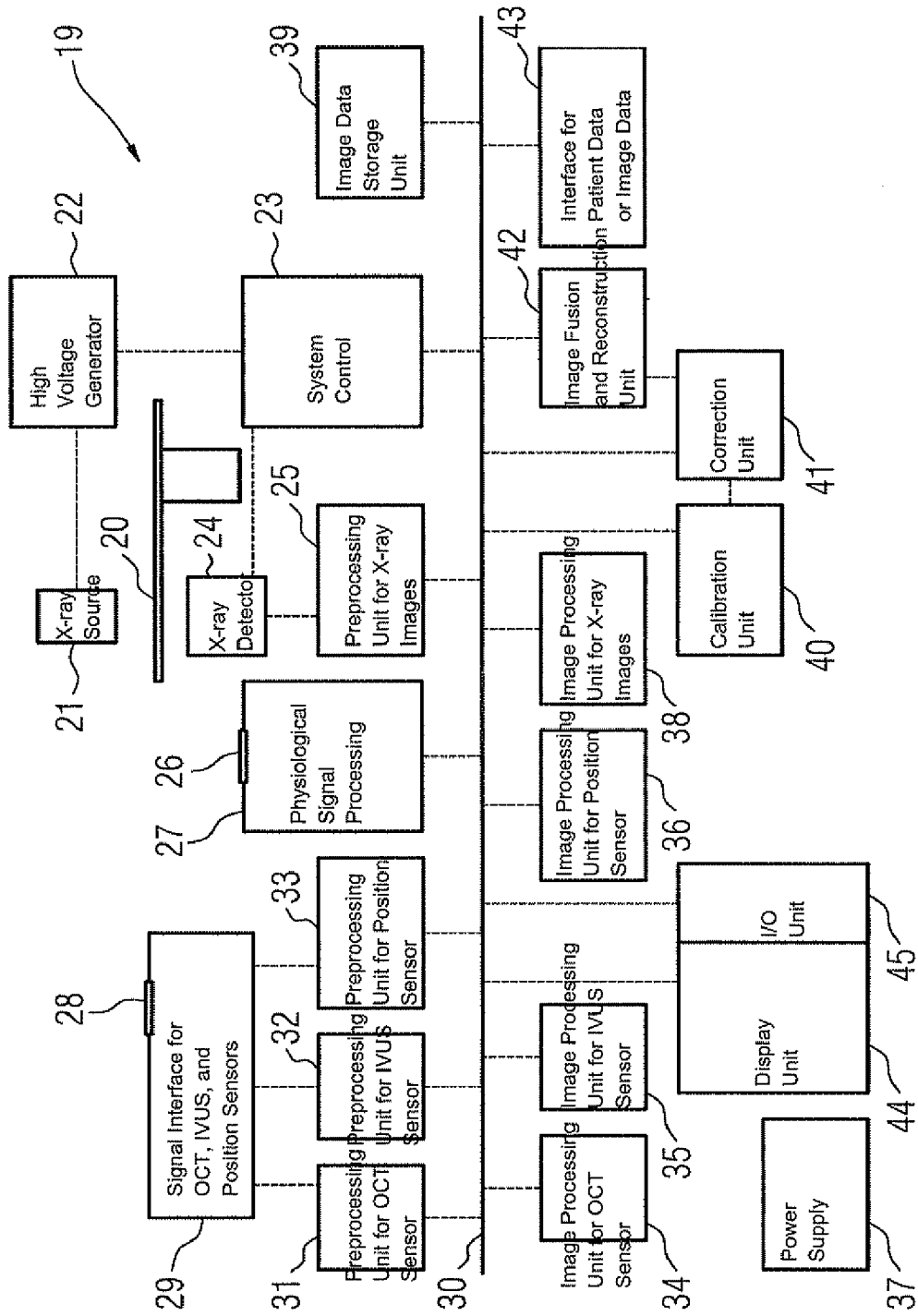
FIG. 3 an inventive treatment unit with a catheter device.

FIG. 1 shows an inventive catheter device 1 which is embodied as an atherectomy catheter. The inventive catheter device 1 features a hollow flexible drive shaft 2 in which an OCT signal line 3 and an IVUS signal line 4 are integrated. In addition a signal line 5 for a position sensor system, which is embodied as an electromagnetic sensor system, is arranged in the flexible drive shaft 2. An IVUS sensor 6 and an OCT sensor 7 are integrated into the front part of the catheter. In the area of the catheter tip 8 is located an opening with a cutter 9, which is embodied as a rotating knife. At the catheter tip 8 is located a light exit window for the OCT sensor 7. Furthermore magnetic sensors 18 of the sensor system are arranged there. These sensors interoperate with a position sensor 10 which is arranged outside the body of the patient. The position sensor 10 is embodied as an electromagnetic sensor.

The drive shaft 2 is surrounded by a catheter sheath 11. Opposite the opening is located an expandable balloon 13 for supporting positioning.

A signal interface and a drive unit 15 are connected via a rotation coupling 16 to the catheter device 1.

With the catheter device shown in FIG. 1 the cutter 9 for performing atherectomy is connected to the OCT sensor 7, the IVUS sensor 6 and position sensors into an integrated unit.

FIGS. 2A and 2B show a second exemplary embodiment of a catheter device.

The same reference symbols are used for those components of the catheter device which correspond to those shown in the first exemplary embodiment.

FIG. 2A shows an imaging-catheter 17 with an IVUS sensor 6, an OCT sensor 7 with viewing window, magnetic sensors 18, position sensors 10, signal lines 4 for IVUS and signal lines 3 for OCT. Likewise a signal interface and a drive unit 15 are provided.

FIG. 2B shows an atherectomy catheter 14 which features a lumen, into which the Imaging catheter 17 is able to be introduced. Like the catheter shown in FIG. 1, the atherectomy catheter 14 has a cutter 9 in the area of the catheter tip 8 as well as a rotatable balloon 13. In the area of the catheter tip 8 the lumen is transparent for OCT and IVUS. Within the catheter 14 is located a hose 46 for a pressure medium of the balloon 13.

The two catheter devices 1, 17 shown in FIGS. 1 and 2 each have an OCT sensor and an IVUS sensor. The OCT sensor delivers especially good images of the local area, the IVUS sensor delivers a good representation of layers further away or deeper down.

The catheter devices 1, 17 are connected to an image processing unit which creates a common image from the images delivered by the two sensors. To do this it uses a section of the image delivered by the OCT sensor for the local area and for the remote area the complementary part of the IVUS image, the two sections are registered with each other by means of the data of the position sensors and fused together into a joint image. In this way sectional images of the vessel being examined are obtained, which can be assigned precisely to a defined position in the body. Computational methods are employed to use the data of the position sensor in order to approximate the center line and the envelope of the vessel being examined. Subsequently the individual sectional images are combined to form a volume data set so that an exact and thus especially realistic image is produced.

In the approximation of the center line of the vessel and the envelope of the vessel the geometrical information of the center line is used and combined with the sensor positions recorded during imaging, which greatly reduces the artifacts in 3D imaging. The 3D co-ordinates of the center line and the sensor positions recorded during imaging are subtracted from one other. The result of the subtraction is then used for each of the recorded 2D images for exact 3D reconstruction. This envelope of the vessel can be used for further stages in processing the image. With the aid of the envelope the 3D reconstructed OCT-IVUS images are registered with other anatomical image data such as from a 3D angiography device of the same vessel section and subsequently fused together.

The position sensors 10 used in the exemplary embodiments of FIGS. 1 and 2 are electromagnetic position sensors to create 3D OCT-IVUS images from 2D OCT-IVUS images. The recording of the orientation and position of the catheter in a three-dimensional co-ordinate system is undertaken by transmit coils in the object and receive coils in the room or conversely with receive coils in the object and transmit coils in the room.

The electromagnetic transmitter or alternatively the electromagnetic receiver can be located in the catheter. Conversely the corresponding electromagnetic receiver or transmitter can be accommodated outside the body. Normally at least one transmitter emitting radiation in the X, Y, Z direction is assigned to a receiver or conversely a receiver with X, Y, Z receive directions is assigned to a transmitter to allow for location in the room. The coils of the electromagnetic position sensors are not arranged exclusively orthogonality to each other, but at any given angle of for example 60°, to achieve a better miniaturization which allows the position sensors to be built into a catheter.

The image information of the catheter which is recorded with the sensors is combined or overlaid with other medical images such as 2D or 3D recordings. The OCT-IVUS images of the catheter are displayed jointly with the x-ray images. This makes the information about the images of the catheter device and the x-ray images visible jointly for the user and makes more rapid and better diagnosis possible. In addition 2D-2D, 2D-3D, 3D-3D and 3D-4D and 4D-4D overlays are possible, in which case the angiographic x-ray images are combined in each case with the images of the catheter device by segmentation, registration and image fusion. Images of the following modalities and methods can be used for overlaying: Sonography including IVUS, radiography, fluoroscopy, angiography, OCT, discrete tomography, Positron Emission Tomography, nuclear medical diagnostics, computer tomography, nuclear resonance tomography including intracardial MR, optical recording including endoscopy, fluorescence and optical markers.

The catheter device is part of a medical examination unit which possesses a functional unit for rectification of movement artifacts which arise as a result of breathing and the movement of the heart and the blood vessels. To rectify the breathing artifacts a breast band can also be used which determines via the appropriate sensors the breathing amplitude and frequency so that the image processing unit can make the necessary corrective calculations in order to calculate out the movement artifacts from the image information.

To increase the location accuracy the transmit coils are operated and evaluated cyclically at specific intervals in time with different frequencies. To avoid sensor artifacts which can be produced by overlaying signals of the individual sensors it is proposed to read out the sensors offset in time and clocked. For example the x-ray detectors and the ECG are not read out if the transmitters of the electromagnetic positioning system are active. The OCT sensors and positions sensors are not read out if the x-ray radiation is active Thus only such signals are ever read out as are not subject to disturbances and do not influence any other active sensors.

The functional units and signal lines are equipped with devices and measures which shield the physiological signals and image signals and the signal processing and signal editing from the magnetic filters of the transmit antennas. To this end the shell of the catheter is coated with a thin film layer made of conductive nanoparticles. Likewise nanoparticles can be used to effect a magnetic shielding.

The catheter shell is provided with a coating which reduces the frictional resistance during guidance through the vessel. This coating can also be based on nanotechnology or alternatively can be made from a silicon material.

To improve the imaging by the IVUS sensor by using ultrasound contrast means the contrast means is introduced directly into the vessel to be examined or the body cavity through a channel in the catheter.

A temperature sensor or a pressure sensor can be arranged in the tip of the catheter to monitor the temperature and the pressure in the vessel or the organ to be examined and treated. The temperature sensor, which is accommodated in the tip of the catheter, enables any possible temperature increase arising as a result of friction to be detected.

FIG. 3 is a schematic diagram of the inventive treatment unit.

The treatment device 19 comprises a catheter device for performing atherectomy. For treatment a patient not shown in FIG. 3 is supported on a patient table 20, radiation is emitted by radiation source 21 in the direction of the patient table 20. The radiation is produced via a high-voltage generator 22 controlled via a system control 23. Opposite the x-ray source 21 is arranged an x-ray detector 24 which in its turn is connected to a preprocessing unit 25 for x-ray images. In addition a connection 26 is provided for physiological sensors, which is coupled to a physiological signal processing 27 in order to control ECG signals or pulse signals or the breathing and the blood pressure of a patient.

The actual treatment is undertaken via a connection 28 for the atherectomy catheter via a signal interface 29 under image monitoring by OCT, IVUS and the electromagnetic position sensor system. In addition there is a connection to the data bus 30. There are also preprocessing units 31, 32 and 33 provided for OCT, IVUS and the position sensors. Associated image processing units 34, 35 and 36 for OCT, IVUS and the position sensors are also connected to the data bus 30. The power is supplied via a power supply unit 37. Furthermore an image processing unit 38 for the x-ray images is connected to the data bus 30, which features a connection to an image data store 39 for archiving and storing the recorded images. A calibration unit 40 as well as an image correction unit 41 enable interference fields or artifacts of the imaging to be taken into account. The images are fused and reconstructed in an image fusion and/or reconstruction unit 42. In addition there is an interface 43 to a patient data or image data system.

The image data obtained from OCT, IVUS and the position sensor system as well as the x-ray images and possible fusion images of the different imaging techniques are shown on a display unit 44 in two dimensions, three dimensions or four dimensions. The display unit 44 is connected to an input 45 for input by a user.

FIG. 4 is a schematic diagram or the sensor read-out of the treatment unit during execution of the inventive method.

A typical execution sequence is as follows: Introducing he catheter under x-ray control, possibly with contrast means, creating the angiographic overview image, creating the images of the position sensors, overlaying the images of the position sensors with the overview angiography by segmentation, registration and image fusion, navigating the catheter based on the images obtained up to the destination position, these steps are in some cases executed in parallel and automatically without the interaction of the user. Once the desired destination position has been reached the flushing fluid for OCT is injected and the stenosis is observed with the OCT-IVUS images in two dimensions or three dimensions at high resolution. Subsequently the OCT-IVUS images are created. Subsequently the OCT-IVUS images are overlaid with the overview angiography by segmentation, registration and image fusion. Subsequently a 3D reconstruction of the OCT-IVUS images is undertaken based on the data of the position sensors. The atherectomy catheter is placed and temporarily fixed for example by inflating the balloon accommodated at the catheter tip. Checking with OCT-IVUS in 2D and 3D, whether the position and location of the atherectomy catheter is correct. Performing the atherectomy, which means shaving off the plaque from the vessel wall with the rotating knife. If a specific amount of plaque is removed, the OCT sensor is used to check this point in the vessel wall. The process is repeated until the plaque is removed at all points. Final check of the atherectomy and removal of the catheter.

The inventive device reduces the number of steps required. The OCT sensor delivers good images in the local area, the IVUS sensor sufficiently good images of tissue layers located further down. The electromagnetic position sensors allow 3D images to be created from the OCT and IVUS images. In addition, after an overview angiography has been carried out, by appropriate utilization of the signals of the position sensors, the passage of the catheter can be mapped solely on the basis of the IVUS, OCT and electromagnetic signals, which means that x-ray radiation can be saved. The system delivers important additional medical information about the arteriosclerotic plaque. In addition it allows the correct position of the tip of the catheter to be better checked. A further advantage with the integration of atherectomy and OCT also lies in the fact that in this case no separate flushing facility has to be provided for OCT, since a flushing means is already used for the drill head.

The sensors of the medical treatment device, which in the exemplary embodiment presented is an x-ray device, are read out partly offset in time and clocked. Initially a system clock is predetermined in which individual system impulses are created, with this pulsed generation being followed by the switching-on of the x-ray radiation and the activation of the magnetic location. After the x-ray radiation is switched off, the x-ray detector readout occurs and at the same time the IVUS data is read out. Subsequently the OCT data is read out, with this occurring at the same time as the readout of the ECG and the data for respiration. This means that the individual sensor is read out or the components of the catheter device are activated in such a way that a mutual fault can be excluded. The time-offset and clocked readout shown here is to be seen as an example for a readout avoiding interference influences.

The invention claimed is:

1. A catheter device for performing an atherectomy in a patient, comprising:
   an atherectomy catheter having a rotating knife like cutter arranged in a tip area of the catheter;
   an OCT sensor arranged in a front part of the atherectomy catheter;
   an IVUS sensor arranged in the front part of the atherectomy catheter;
   a position sensor interoperated with the OCT sensor and the IVUS sensor; and
   an image processing unit connected with the OCT sensor, the IVUS sensor and the position sensor via a data bus, the image processing unit configured to create a combined image based on data from the sensors;
   wherein the position sensor is an electromagnetic sensor which comprises a transmit coil arranged in the atherectomy catheter and an external receiver coil, or an external transmit coil and a receiver coil arranged in the atherectomy catheter;
   and wherein the OCT sensor or the IVUS sensor is arranged on one side relative to a longitudinal axis of the atherectomy catheter.

2. The catheter device as claimed in claim 1, wherein the position sensor is arranged at the tip area of the atherectomy catheter.

3. The catheter device as claimed in claim 1, wherein the atherectomy catheter is mechanically controlled via pulling wires that steer the tip of the catheter.

4. The catheter device as claimed in claim 1, further comprising a permanent magnet or an electromagnet arranged within the catheter that controls a catheter motion in cooperation with an external magnetic field.

5. The catheter device as claimed in claim 1, wherein the external receiver coil or the receiver coil arranged in the atherectomy catheter comprises an iron core and is functioned as a receiving antenna or an electromagnet for a magnetic navigation.

6. The catheter device as claimed in claim 1, wherein the coils are arranged orthogonally in respective to each other or at a given angle.

7. The catheter device as claimed in claim 1,
   wherein the OCT sensor and the IVUS sensor are configured to be rotated separately or together around a longitudinal axis of the atherectomy catheter, or
   wherein the atherectomy catheter is configured to be pushed or pulled by a drive unit at a definable speed.

8. The catheter device as claimed in claim 1, further comprising a 3-D image processing unit that produces a 3-D image of the patient,
   wherein the image processing unit approximates a center line or an envelope of a part of a body of the patient to be examined,
   wherein the 3D image of the patient is recorded by the atherectomy catheter,
   wherein the 3D image is registered and fused by the image processing unit based on the approximated center line or envelope with other anatomical image data of the patient, and
   wherein the 3D image recorded by the atherectomy catheter and the anatomical image data is transferred to a common coordinate system.

9. The catheter device as claimed in claim 1, further comprising a recording device,
   wherein a movement artifact caused by a breathing or a movement of an organ of the patient is determined by recording a frequency or an amplitude of the movement, and
   wherein the movement artifact is corrected.

10. The catheter device as claimed in claim 1, wherein the sensors are configured to read out offset in time to avoid a mutual interference.

11. The catheter device as claimed in claim 1, wherein the atherectomy catheter comprises a coating made of conductive antiparticle to provide shielding from an electromagnetic field.

12. The catheter device as claimed in claim 1, wherein the atherectomy catheter and the sensors are electrically decoupled.

13. The catheter device as claimed in claim 1, wherein the atherectomy catheter comprises an x-ray marker.

14. The catheter device as claimed in claim 1, wherein the atherectomy catheter is coated by a coating to reduce a friction resistance.

15. The catheter device as claimed in claim 1, wherein the atherectomy catheter comprises an inflatable balloon to support positioning.

16. The catheter device as claimed in claim 1, wherein the atherectomy catheter comprises a temperature sensor or a pressure sensor arranged at a tip area of the atherectomy catheter.

17. A medical treatment unit for performing an atherectomy procedure in a patient, comprising:
- a medical image device which generates an image data of the patient;
- a catheter device integrated with the medical image device comprising:
  - an atherectomy catheter having a rotating knife like cutter arranged in a tip area of the catheter,
  - an OCT sensor arranged in a front part of the atherectomy catheter,
  - an IVUS sensor arranged in the front part of the atherectomy catheter,
  - a position sensor interoperated with the OCT sensor and the IVUS sensor; and
- an image processing unit connected with the OCT sensor, the IVUS sensor, the position sensor, and the medical image device via a data bus, the image processing unit configured to create a combined image based on the image data from the medical image device and data from the sensors.

18. A method for creating an examination image in an atherectomy procedure in a patient, comprising:
- inserting an atherectomy catheter into a body of the patient, the atherectomy catheter comprising a rotating knife like cutter arranged in a tip area of the catheter, an OCT sensor, an IVUS sensor and a position sensor;
- processing and combining image data obtained from the OCT sensor, the IVUS sensor and the position sensor by an image processing unit; and
- creating the examination image based on the processed and combined image data.

* * * * *